United States Patent [19]

Wagner

[11] 4,284,077

[45] Aug. 18, 1981

[54] SUCTION INJECTOR HAVING AN ADJUSTABLE DOSING DEVICE

[76] Inventor: Wolfgang Wagner, Exerzierstrasse 1, 1 Berlin 65, Fed. Rep. of Germany

[21] Appl. No.: 93,615

[22] Filed: Nov. 9, 1979

Related U.S. Application Data

[60] Division of Ser. No. 933,136, Aug. 14, 1978, abandoned, which is a continuation-in-part of Ser. No. 793,951, May 5, 1977, Pat. No. 4,114,619, which is a continuation-in-part of Ser. No. 634,741, Nov. 21, 1975, abandoned.

[30] Foreign Application Priority Data

Nov. 19, 1974 [GB] United Kingdom ............... 49989/74
Nov. 19, 1974 [GB] United Kingdom ............... 49990/74

[51] Int. Cl.³ .............................................. A61M 5/00
[52] U.S. Cl. .................................. 128/215; 128/218 A
[58] Field of Search ............... 128/215, 218 R, 218 A, 128/218 F, 216, 276, 302

[56] References Cited

U.S. PATENT DOCUMENTS

| 1,934,046 | 11/1933 | Demarchi | 128/215 |
| 2,743,723 | 5/1956 | Hein | 128/215 |
| 3,122,138 | 2/1964 | Geary | 128/215 |
| 4,114,619 | 9/1978 | Wagner | 128/215 |

Primary Examiner—John D. Yasko
Attorney, Agent, or Firm—Michael J. Striker

[57] ABSTRACT

The suction injecting unit comprises a tubular housing adapted for receiving a disposable container for receiving the medicine to be administered, and having at one end a socket for exchangeably supporting a cannula and a removable suction cup, and at the other end a piston combined with a dosing mechanism that allows only a preset stroke of the piston. A suction apparatus controlled preferably by a pressurized gas is attached to the housing and is provided with control valves to successively establish an underpressure in the suction cup, and to maintain the underpressure in the cup while moving the piston about a predetermined stroke.

15 Claims, 16 Drawing Figures

FIG. 4
(B-C)
FIG. 5
(B-D)
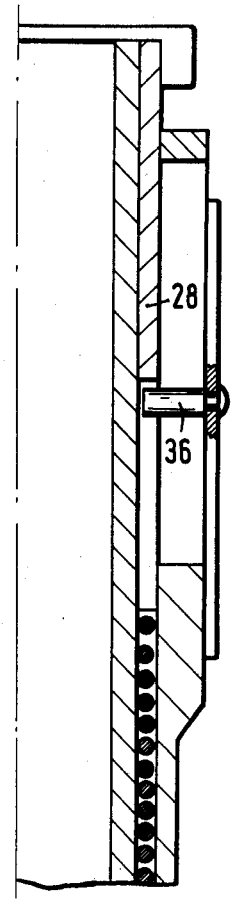
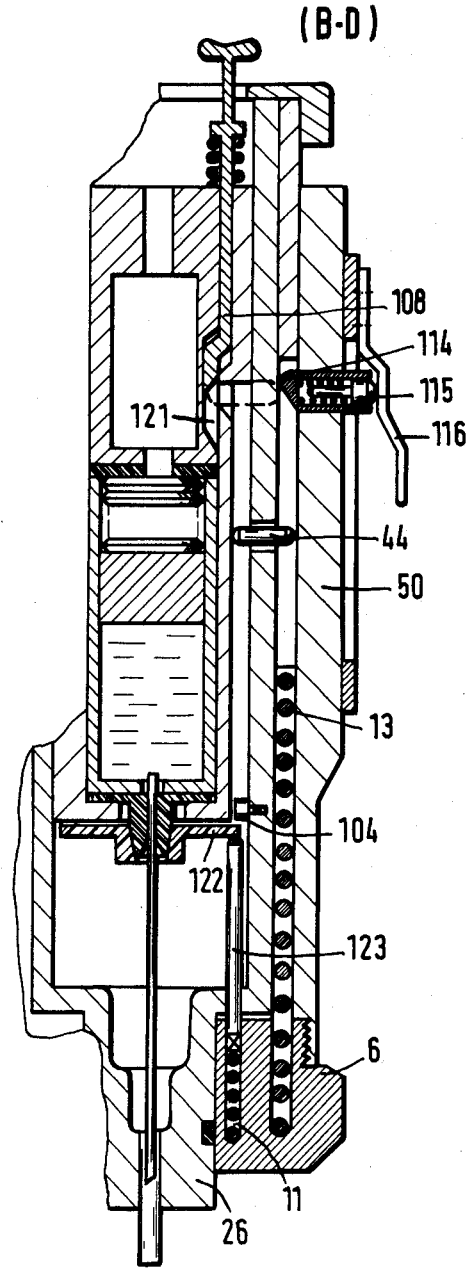

(B-F)

(B-G)

SUCTION INJECTOR HAVING AN ADJUSTABLE DOSING DEVICE

CROSS-REFERENCE TO RELATED APPLICATIONS

This is a division, of application Ser. No. 933,136, filed Aug. 14, 1978 now abandoned, which in turn is a continuation-in-part of my copending patent application Ser. No. 793,951, filed May 5, 1977, now U.S. Pat. No. 4,114,619 which in turn is a continuation-in-part of my application Ser. No. 634,741, filed Nov. 21, 1975, now abandoned, and the entire disclosure of which is herewith incorporated by reference. This application is also related to my copending patent applications Ser. No. 618,686 filed Dec. 21, 1975, Ser. No. 634,742, filed Nov. 21, 1975, and Ser. No. 639,685, filed Dec. 8, 1975, all of whose disclosures are also herewith incorporated by reference.

BACKGROUND OF THE INVENTION

The invention relates generally to the medicine technology, and more particularly, it relates to the injection therapy or subcutaneous extration of samples.

Devices, which drive injection cannulas into the body by sucking first the skin against the cannula tip are known from prior art. With the suction injection bones, vessels and nerves are not touched and the medicine inflow into the tissue is facilitated and pain is avoided.

The known devices of this type however have the disadvantage that they are relatively bulky and are difficult to be operated by the patient himself. Small suction injectors using an exchangeable syringe have the difficulty to locate exactly the point on patients' skin where the puncture is to be made and the charging of the syringe with the medicine is frequently a cumbersome operation. The small prior art suction injectors do not provide means for adjusting an exact dose of the medicine to be administered.

SUMMARY OF THE INVENTION

It is therefore a general object of the present invention to overcome the aforementioned disadvantages.

More particularly, it is an object of the invention to provide an improved suction injector which can be used for administering a succession of doses from a single charge of the medicine in the container.

An additional object of the invention is to provide an improved suction injector which can be manipulated by one hand only.

Further object of the invention is to provide a dosing mechanism for the suction injector that forms therewith a compact unit and which allows a repeated injection of a predetermined dose without any adjustment of the dosing mechanism.

Furthermore, an object of the invention is to provide a suction injector having a dosing mechanism in which the cannulas can be easily exchanged and the disposable container for medicine can be easily replaced.

In keeping with these objects and others which will become apparent hereafter, one feature of the invention resides, in a suction injector having a dosing mechanism in a combination which comprises a tubular housing for receiving a separate container for the medicine to be administered, the container having at one end a socket for supporting a cannula and at the other end being adapted for receiving a plunger, the housing being provided at one end with a suction cup surrounding the cannula and at the other end with a spring loaded dosing mechanism cooperating with the piston in the cannula in such a manner as to allow a predetermined stroke of the piston only, the setting mechanism being attached to the housing and connected to the dosing device in the housing through a hermetically sealed cup, underpressure producing means including either a hand-operated vacuum pump or a pressure fluid operated stream pump communicating with the suction cup via at least one valve controlled conduit. The strokes of the piston in the medicine container can also be either hand-operated or operated by a pressure fluid from the underpressure producing means.

In one embodiment, the movement of the piston of the hand-operated suction pump takes place downstream the cannula socket and is sealingly movable along a tube attachable to the cannula needle. The exchange of the cannula is effected by releasing a motion-limiting arresting means and the cannula attachment tube together with the medicine container can be shifted so far that the cannula attachment tube projects above the rim of the suction cup.

The discharge of the medicine can be made by means of an impermeable elastic membrane. Preferably, a folded bellows is arranged between the pressure gas and the medicine in the container. The bellows protects the medicine from the outer atmosphere when a series of containers with the liquid medicine is mechanically transported within the housing of the injector.

The dosing can be carried out also in such a manner that the piston in the medicine container is coupled to telescopically connected tubes that step by step move the piston toward the discharge opening.

The exchange cannulas in another embodiment is facilitated by providing a movable wall portion in the suction cup that can be displaced as far as to the cannula socket.

In a further modification, arresting means are provided that cooperate with the piston of the suction pump that allow the injection only then when the skin has been sucked into the suction cup and penetrated by the tip of the cannula.

In one modification of the dosing mechanism, a rod is employed that normally is pivotably arranged along the housing for the medicine container and for each injection is tilted from its rest position parallel to the housing into an axial position in contact with the piston of the medicine container and thereupon is connected to an axially movable dosing sleeve on the surface of the injector housing, the connection being made preferably by means of a clamping device.

Instead of a suction piston movably arranged within the suction cup, the space around the cannula within the suction chamber can be also provided with a folded bellows and the cannula is allowed to penetrate in axial direction through the bellows when the suction cup is in evacuated condition. The cannula needle can be provided with a protective sleeve of a synthetic material that projects from the suction cup and is removed before application of the injector.

To control the depth of penetration of the cannula into the patient's body one or more steps on the cannula needle are provided or one or more ring is attached to the sealing margin of the suction piston. For this purpose, also an adhesive layer between the protective sleeve and the cannula shaft or needle can be employed that by applying an increased force is released. The passage between the medicine container and the cannula shaft can be sealed by means of a membrane that is punctured by means of the liquid medicine pressure against the other end of the cannula.

In a preferred embodiment, a plurality of cannulas are stored in a separate compartment and are transported toward the socket in the medicine container on rails and a separate pushing device. The plunger of the pushing device is preferably spring-biased and is connected with the protective sleeve of the cannula shaft that acts as a stop for the movement of the plunger so that the cannula is made automatic.

In another modification of the suction pump, the underpressure is generated in a jet pump in which a stream of pressurized gas from a pressure gas capsule exhausts air from the suction cup and the underpressure in the suction cup is maintained by means of a one-way valve open during the administering of the medicine.

In another embodiment of the dosing device the piston in the medicine container is provided with a spring-biased dosing rod the movement of which within the piston is adjustable from the outside and is connected via a spring biased yoke and a spring guided by the yoke to a winding roller attached to the outer surface of the injector housing. The length of the string that corresponds to the desired dose is determined by the adjusted length of the spring-biased dosing rod within the piston rod by the winding roller.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawing.

BRIEF DESCRIPTION OF THE DRAWING

FIGS. 3, 3a and 3b, to 9 show a mechanically operated suction injector with a dosing mechanism according to this invention;

FIGS. 10 and 3a-3b is a modification of the suction injector of FIG. 22 with the possibility of exchanging the cannula;

FIG. 1 shows an embodiment of the suction injector having a dosing device that includes a disposable cylindrical medicine container 3 in which a piston 1 is sealingly arranged for sliding movement to compress the liquid medicine against the discharge opening at the lower end of the container 3. The upper part of the piston 1 is covered with a folded membrane 52 that is attached to the upper rim of the container 3 by means of a sealing ring 61 and compressed by means of a closure cap 5. The closure cap 5 is provided with a lateral flange against which a screw ring 62 engaging an outer thread provided on the top part of the injector housing 30 abuts and sealingly closes the central boring in the housing 30. The other end of the folded membrane projects into a blind boring provided in the piston 1 and is secured in position by means of a threaded holding piece 63 that engages an internal thread in the blind boring in the piston 1. The holding piece 62 is provided with a center boring adapted for guiding a pin 64 the lower end supports a spring plate and the upper end of which that projects into the boring in the holding piece 63 is provided with an eyelet to which an end portion of a string 33 is attached. The bottom of the holding piece 63 counteracts a biasing spring 50 that rests on the spring plate at the end of the pin 64. The dosing mechanism further comprises a swingable yoke 35 for guiding the string 33 that leads through a sealed boring in the closure cap 5 and a cover cap 111 and is deviated in a guiding groove in the yoke 35 toward a winding roller 68. The swingable yoke 35 is firmly attached to one end of a rod that is guided in a boring provided in a projecting arm of the housing 30. The other end of the rod is provided with threads on which an adjustable stop nut 34 is screwed and forced in abutment with the lower surface of the projecting arm of the housing 30 by means of a spring 66 extending between the upper surface of the arm and yoke 35. Below the nut 34 the rod is provided with an annular groove through which passes a transverse bolt the outer end of which supports for rotary movement the winding roller 68 on which the other ends of the string 33 is coiled. The other projecting end of the transverse bolt contacts a dosing scale 55 extending between the adjustable stop nut 34 and another projecting arm 37 located below the threaded end of the yoke rod and being provided with a freely rotatable nut 67 adapted for engaging the threaded end of the yoke rod. The projecting other arm is provided with an upwardly directed stop member that abuts against a knurled head of the roller 68 when the yoke 35 with its rod is compressed against the spring 66 to engage the nut 67.

Figure 1:
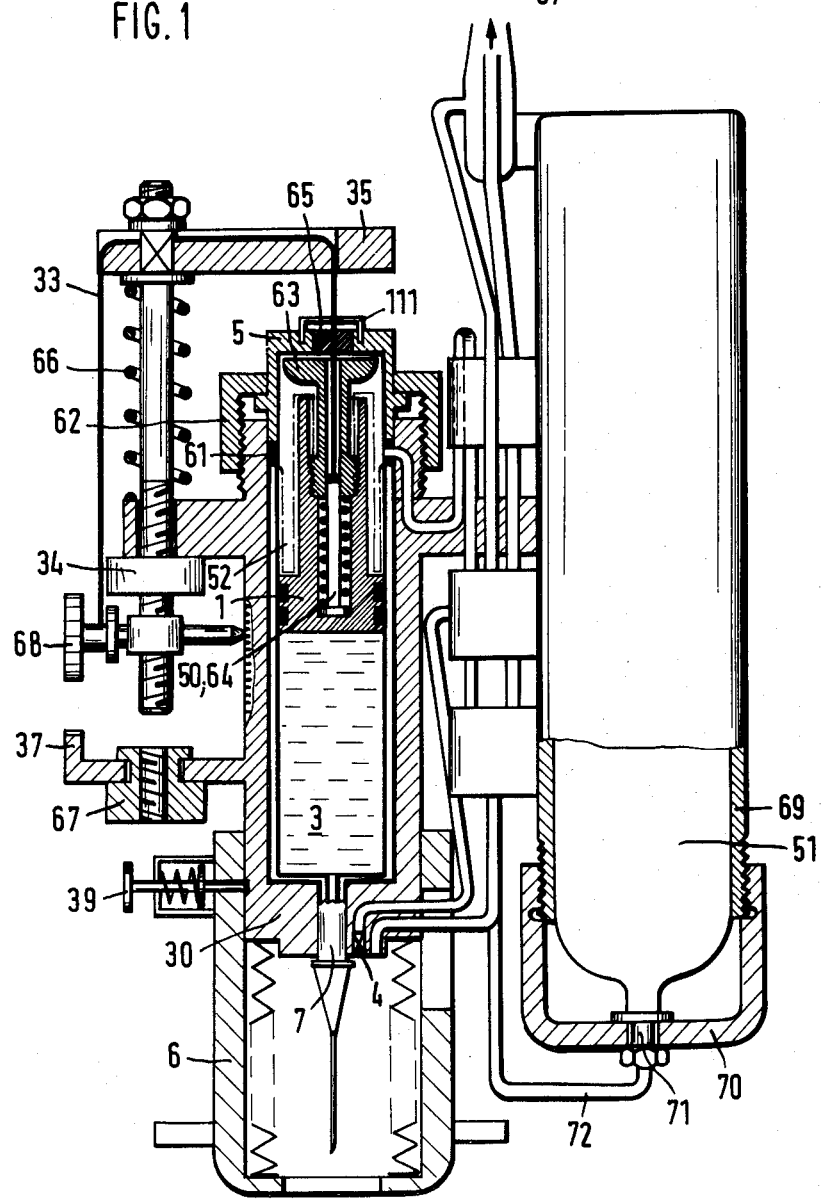
FIGS. 1 and 2 show in a sectional view a pneumatically operated suction injector having a dosing mechanism according to this invention.

The lower part of the housing 30 for accommodating the medicine container 3 supports a suction cup 6 that is attached thereto by means of an arresting mechanism 39.

The actual limit for the suction cup forms bellows 8 that extends within the suction cup 6 and rests upon a narrow annular surface at the end of the housing 30 that surrounds the short annular socket 7 and extends to the lower inwardly directed annular surface on the suction cup 6.

The suction cup 6 defines a center opening that is spaced a certain distance from the tip of the cannula when attached to the socket 7.

Figure 2:
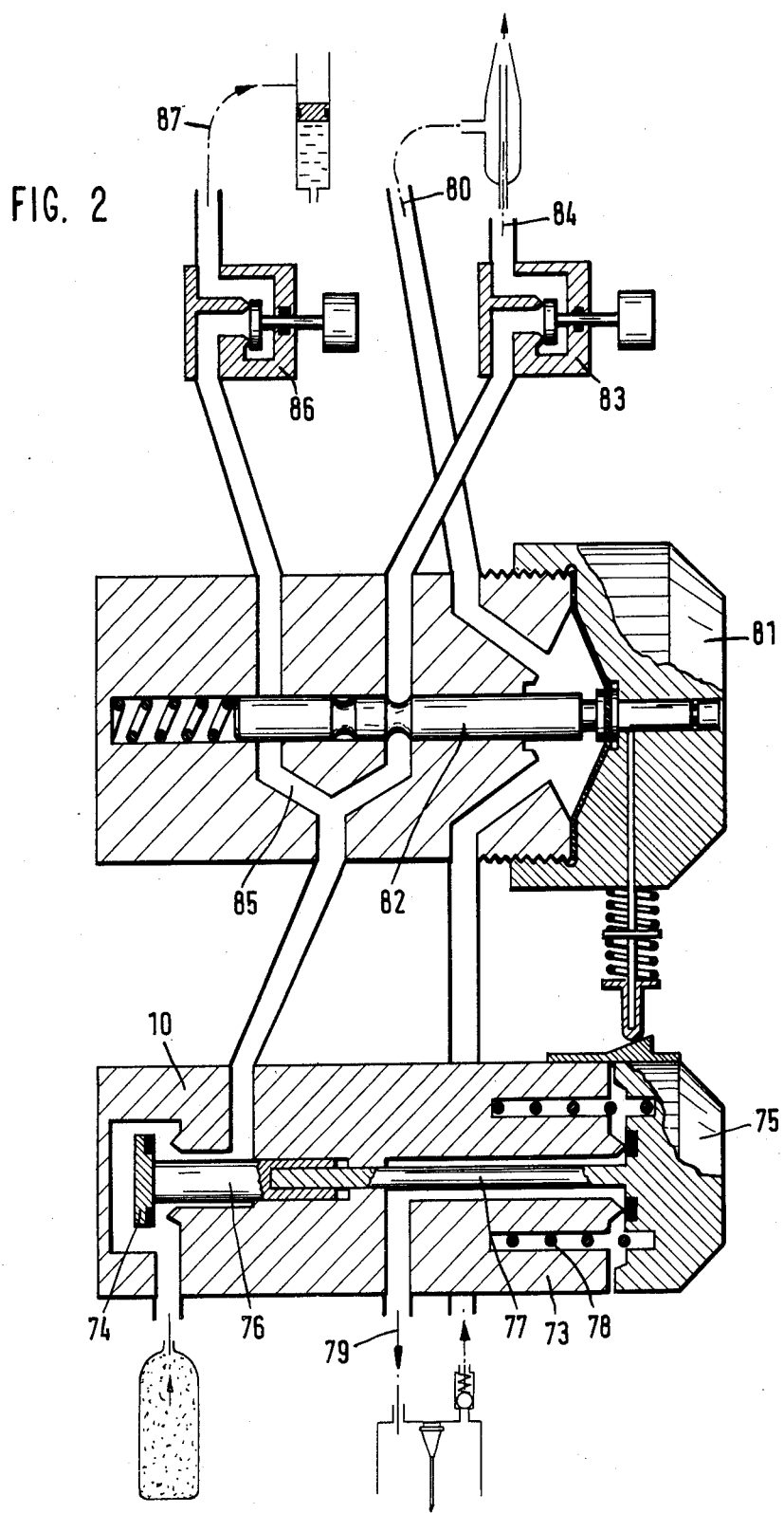
Figure 3:
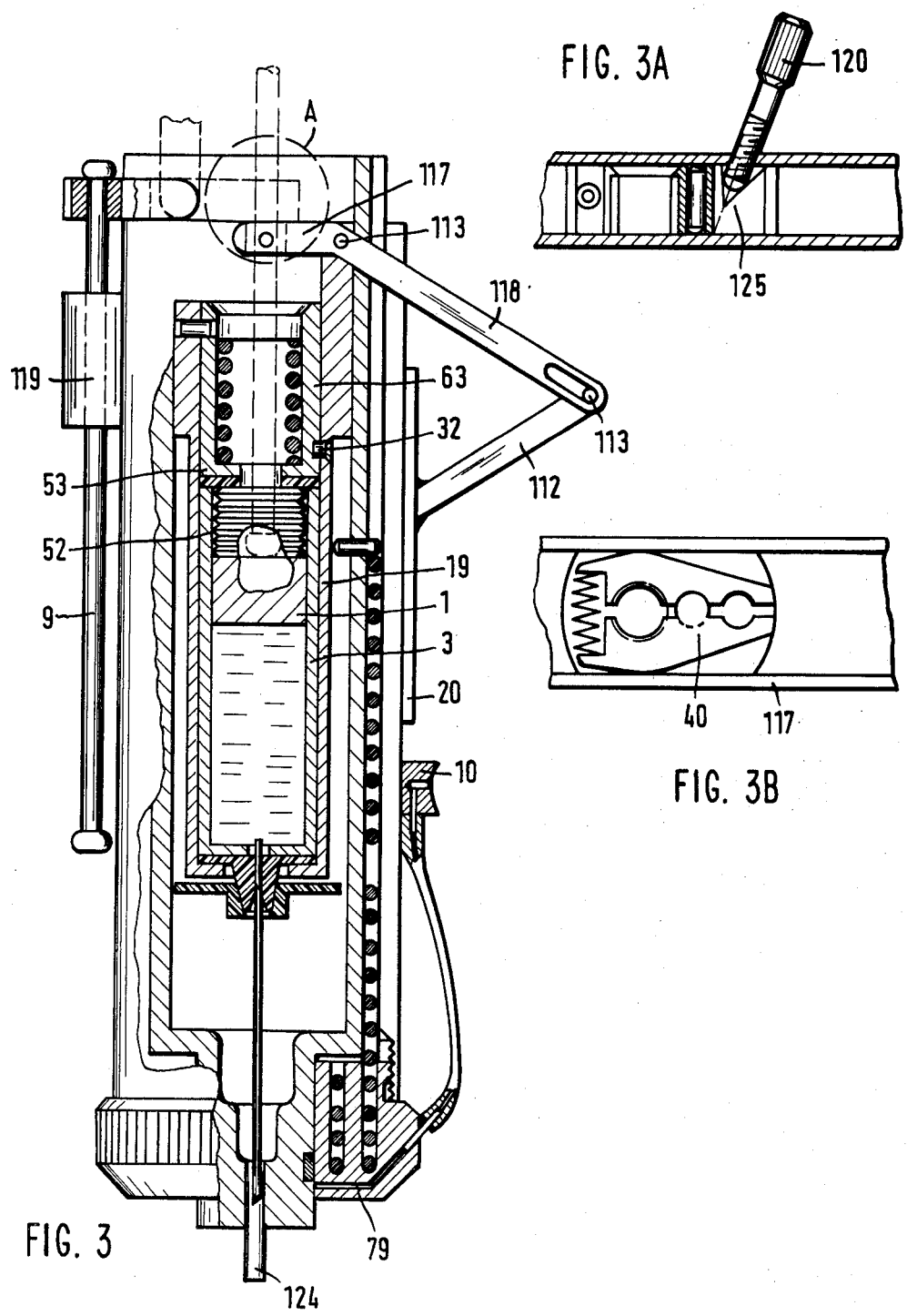

According to one feature of this invention, a receptacle 69 for accommodating a pressure gas container 51 is arranged parallel to the injector housing 30 and is attached thereto by means of clamps held together by screws 37. The receptacle 69 further supports control valves and suction pump extending in the gap between the receptacle 69 and the injector housing 30. The arrangement of the control valves is illustrated in greater detail in FIG. 2. The pressure gas container 51 including compressed $CO_2$, nitrogen or other suitable gas or gas mixture has an outlet sealed by a soft metal. Upon insertion in the receptacle 69, the soft metal seal is opened by a pointed hollow bolt 71 secured to a removable threaded lid 70 and connected through a supply hose 72 to the main pressure control valve 73. The main pressure valve 73 includes a hand-operated control knob 75 that is connected via a rod 77 to a sealing plate 74 that opens a passage 87 opening into the pressure chamber between the folded membrane 52 and the sealing closure cap 5 in the housing 30, thus moving the piston 1 against the cannula 7. The control knob 75 in the main pressure control valve 73 is normally loaded by a spring 78 to take a position in which the sealing plate 74 is closed and a conduit 78 connecting the suction cup 6 with the outer atmosphere is opened. A suction selector valve 81 includes a branch conduit 85 connecting the pressure gas conduit from the main control valve 73 to an outlet nozzle 84 connected to a jet suction pump 89. The control knob 75 closes when actuated a pressure release conduit 79 connecting the suction cup 6 with the outer atmosphere. The underpressure created in the pump 89 is applied via a conduit 80 to a diaphragm-controlled pressure chamber in suction selector 81 and a one-way valve 88 into the suction cup 6. The suction selector 81 includes a selector plunger 82 connected to the membrane in the pressure chamber of the selector 81 and being normally pressed against the membrane by a pressure spring. The plunger 82 is provided with annular recesses that cooperate with the branches of the conduit 85 in such a manner that the plunger 82 first directs the pressure gas through a pressure reducing valve 83 into the jet pump 89. Upon actuation of control knob 75 of the main valve 73, a spring loaded pin 59 following a cam on the control knob 75 connects the control knob 75 to the end portion of the transverse plunger 82 in the suction selector 81 so that the latter is arrested in its suction position.

Referring back to FIG. 1, a cover cap 111 is placed on a seal 65 around the string 33. As mentioned previously, the string is guided in a guiding groove on the yoke 35 toward the dose setting device 67.

To prepare the suction injector of this invention for its function, the closure cap 5 is first unscrewed, the holding piece 63 together with pin 64 and spring 50 are disengaged from the interior of the piston 1 and a new medicine container with a new piston 1 is inserted into the central boring in the injector housing 30. Thereafter, the closure cap is secured in position by means of the screwing 63 and sealingly compressed against the rim of the housing 30 by means of the sealing ring 61.

The threaded lid 70 is then unscrewed from the receptacle 69, a new pressure gas container 51 is inserted into the receptacle 69 and the lid 70 is screwed on the thread on the receptacle 69 until the pointed hollow bolt 71 penetrates through the soft metal seal of the container 51.

Thereafter the stop nut 34 in the dosing mechanism is turned on the thread of the yoke rod until a length of the string 33 corresponding to the desired stroke of the piston 1 is uncoiled from the roller 68 while the yoke 35 keeps the string 33 in a perpendicular position toward the piston 1. Thereupon the yoke 35 is compressed until the threaded end of the yoke rod engages the freely rotatable nut 67 so that the yoke is held in the compressed position. In this position the spring-loaded pin 64 draws a section of the string 33 corresponding to the adjusted stroke of the piston, into the boring of the holding piece 63. By turning the nut 67 on the projecting arm 37, the yoke 35 compresses the cover cap 111. At the same time, the upwardly directed end portion of the arm 37 engages the knurled edge of the roller 68 and thus holds the same in a fixed position. Thereafter, cover 12 is removed, the locking member 39 is released and the bellows 8 within the suction cup 6 is shifted upwardly until it abuts on the cannula socket 7. Thereafter the cannula is inserted on the socket 7 and the suction cup is again pulled upwardly until the arresting mechanism 39 locks the latter in a fixed position relative to the housing 30.

Thereafter the rim of the suction cup 6 is applied to the skin of a patient and the control knob 75 is activated. In doing so, the sealing ring on the inner surface of the knob 75 first closes a valve seat for the pressure relieving conduit 79 and the valve pin 76 displaces the valve plate 74 from the pressurized gas conduit 76 so that pressurized gas from the supply hose 72 is applied through an annular groove in the plunger 82 in the suction selector 81 and a pressure reducing valve 83 into a nozzle 84 of a jet pump 89 thus creating an underpressure that is applied through a suction conduit 80 and the one-way valve 88 into the suction cup 6. Due to this under-pressure, the skin of the patient is sucked into the cup 6 and punctured by the cannula. With increasing suction, the under-pressure causes movement of the membrane in the control pressure chamber in the suction selector 81 and the plunger 82 connected to the membrane is moved to the left against the biasing spring so that the supply of the pressure gas into the jet pump 89 is closed and the branch conduit 85 connecting the pressurized gas into the pressure space above the piston in the housing 30 becomes opened. In reducing the suction in conduit 80 the pressure in conduit 80 increases and closes the one-way valve 88 so that under-pressure in the cup 6 is maintained. The pressure in the pressure space above the piston 1 moves the piston downwardly until the spring plate at the end of the dosing pin 64 compresses the spring 50 against the holding piece 63 and spring 33 prevents further movement of the piston 1. The spring biased pin 59 arresting the plunger 82 of the suction selector 81 in the meantime engages an annular groove at the end of the plunger 82 and thus prevents after the interruption of the suction the displacement of the plunger 82 to the right and the activation of the jet pump 89. Only after the control knob 75 is released, spring 78 opens the suction cup through conduit 79 to the outer atmosphere, the plate 74 closes the supply of pressurized gas and the clamp connected to the control knob 75 allows the arresting pin 59 to disengage the groove on the transverse plunger 82 and allows the return of the membrane into its normal position.

Figure 6:
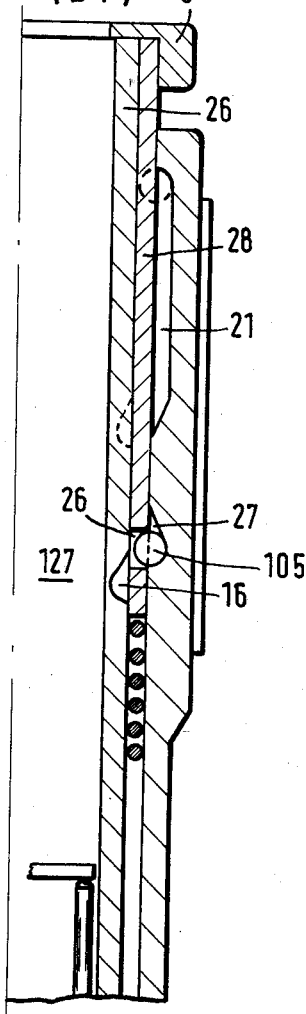
Figure 7:
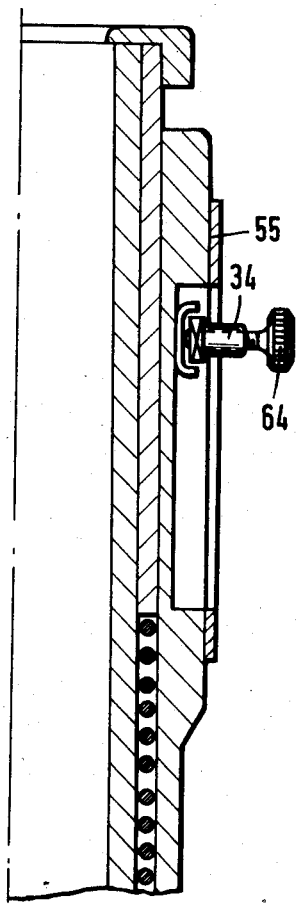

Another embodiment of the suction injector having a spring operated dosing device is illustrated in FIGS. 3 to 9. Similarly, as in the preceding example, disposable medicine container 3 with a cup-shaped piston 1 is inserted in a central boring of a tubular sleeve 19. A folded membrane in the form of bellows 52 is arranged on the upper surface of the piston 1 and is urged by sealing ring 53 and a holding piece 63 against the rim of the medicine container 3. The holding piece 63 is spring-biased by a spring 61 that rests on a displaceable cover cap 111 that in turn abuts on a fork 117 that supports a clamping jaw 40 for clamping a dosing rod as it will explained below. The clamping jaw 40 is controlled by a control screw 120 that moves a wedge-shaped member 125. The dosing rod 9 is shiftably arranged in a boring at the end of a tiltable arm pivotably supported on the top part of the tubular sleeve 19. In the rest position, the arm 35 is tilted so that the rod 9 extends parallel to the outer sleeve 50 and is clamped in clamps 119. In activated position, the arm 35 is turned over 180° so that the rod is in alignment with the center of the piston 1. In this position, it passes through the clamping jaw 40 that, as mentioned above, is held in the form 117 that is secured to a swingable arm 118 pivotably and shiftably supported by means of a pivot pin 113 on a projecting fixed arm 112 secured to a rotatable dosing sleeve 20 arranged on the housing sleeve 50. The dosing sleeve 20 is provided with an inwardly projecting carrier bolt 36 (FIG. 4) that is guided in a slit provided in a carrier sleeve 28 disposed adjacent the inner wall of the housing sleeve 50 and being spring biased upwardly by means of a spring 13 seated in a recess in the suction cup 6. As shown in FIG. 7, the movement of the dosing sleeve 20 is limited by a stop member 34 that is movably arranged in a short longitudinal slit of the dosing sleeve 20 and includes a tubular piece having internal threads for engaging a threaded pin the end of which has a sliding shoe 101 (FIG. 8) that can be applied against a strip-like clamping spring 96 in an axial groove of the housing sleeve 30 and moved along a dosage scale 55 along the slit in the dosing sleeve 20.

A carrier bolt 44 supported in an actuation sleeve 26 is removed from the space of the spring 13 by means of a sliding wedge 114 arranged above the bolt 44 at a distance of one stroke of the piston 1; the sliding wedge 114 is movable within a transverse boring in the housing sleeve and is provided with a recess for accomodating a spring biased counterpin 115 projecting through a slit in the dosing sleeve 20 against respective control surface of a cam 116. In order that the carrier bolt 44 might be displaced from the area of the carrier sleeve 28, a niche 121 is provided in the tubular sleeve 19 and in the holding member 63. A spring biased wedge-like slider 108 engages at one end the niche 121 and projects upwardly above the fork 117 of the setting yoke 35. The inner surface of the actuation sleeve 26 supports stop screws 104 for displacing a cone plate 122 against three pins 123 that rest on a spring 8 located in a recess in the suction cup 6. The cone plate 122 surrounds the conical circuit 7 for the cannula. The suction cup 6 is screwed at the end of the tubular housing 50 and includes a pressure relieving conduit 79 that via a hose and a pressure relieving valve connects the suction cup with the outer atmosphere. The cannula shaft is provided with a protecting sleeve 124.

As seen from FIG. 6, an axial recess 21 in the tubular housing sleeve 30 serves for rolling up a ball 105 and a drop-shaped arresting recess 16 on the outer surface of the actuation sleeve 26 for the suction piston communicates with an opening in the carrier sleeve 28 with an opposite drop-shaped arresting recess 27 in the inner surface of the housing sleeve 30.

A cover cap 5 is secured to the upper rim of the actuation sleeve 26 and the carrier sleeve 28.

Figure 8:
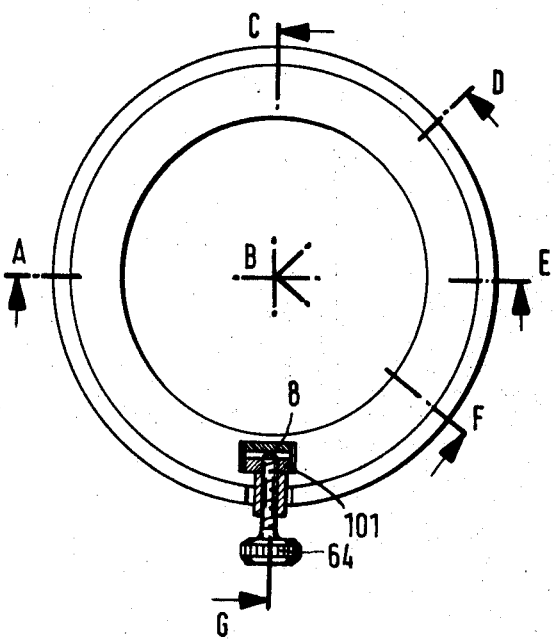
Figure 9:
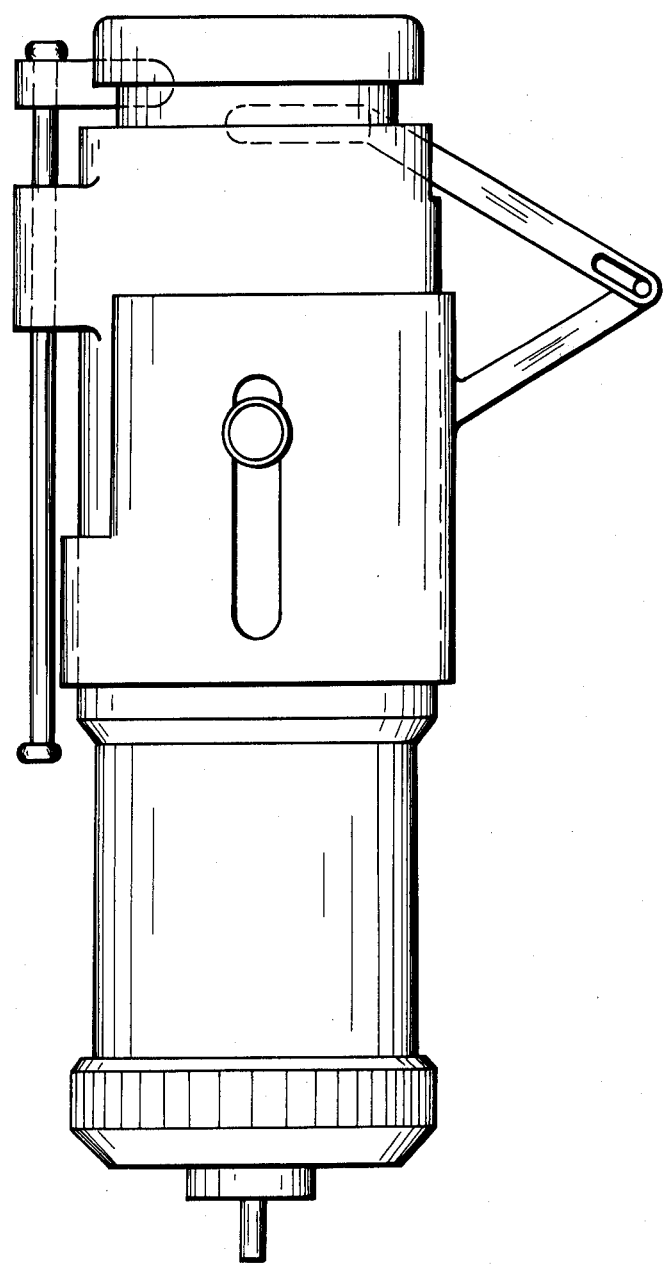

To operate this embodiment of the dosing suction injector, the projecting wedge-like slider 28 is pulled out, the setting yoke 35 is turned up about the hinge of the swinging arm 112 and the holding piece 63 is removed. Thereafter the medicine container 3 is inserted into the guiding sleeve 19, the holding piece is screwed into the upper portion of the guiding sleeve 19, the setting yoke 35 is returned to its position against the holding piece 63 and the rotary axle 113 is pushed in. Thereafter the dosing rod 9 is retrieved from the clamping means 119 by rotating the swinging arm 118 and tilting about 180° so that the rod 9 can be pushed through the clamping jaw 40 in the fork 117 and abuts with its end on the upper surface of the piston 1 within the bellows. The dose adjustment is made by shifting the stop 34 around the dosing scale and by arresting the sliding shoe 101 by screwing the pin 64. Thereupon the tightening screw 120 in the fork 117 is tightened up so that the clamping jaw 40 firmly grips dosing rod 110 and compress the same against a transverse track in horizontally shiftable sliding shoe 125 in the fork 117. The dosing rod is provided with a soft coating that maintains traces of clamping to indicate the stroke of the piston. Thereupon the slider 108 is depressed and thus the carrier bolt 44 is removed and the actuation sleeve connected to the suction piston is released. The suction cup is first placed on a solid support and by compressing the cover plate 5 the driving spring 13 is tensioned. As seen from FIG. 6, the carrier sleeve 28 for tensioning the driving spring 13 provided with a slit for allowing the movement of the wedge slide 114 (FIG. 5), takes along the ball 105 between the arresting recess 27 and the axial groove 21 in the tubular housing 50 until the ball is discharged through the opening in the carrier sleeve 28 into the arresting recess 16 in the actuation sleeve 26 and in this manner it is lowered about the maximum length of travel of the dosing sleeve 20 and then by taking along the suction piston once more about the height of a piston stroke until the balls 105 used for further lowering of the arresting recess 116 are discharged in the arresting recess 126 in the tubular sleeve 50 and come to rest, whereas the suction piston projects above the rim of the suction cup (FIG. 9). If a cannula is introduced into the suction piston, the end of the cannula is depressed into the elastic seal of the cannula socket 7 when due to the compression of the cap 5 the conical plate 152 is lifted. By the action of the pins 123 the cannula shaft is sealingly compressed in the cannula socket and held in position. If the injector is now applied on the skin, the suction piston 26 is first retracted to the level of the rim of the suction cup, bolts 105 are forced into the arresting recess 16 and the movement of the driving spring 13 is released. By compressing the valve 10 the pressure relieving conduit is closed. By lifting the actuation sleeve 26 and by rolling the balls in the axial groove 21 in the housing sleeve 50 the suction piston is lifted and a partial under-pressure is created above the skin so that the skin is sucked into the cup 6 and penetrated by the tip of the cannula. As seen from FIG. 5, the carrier bolt 44 transmits the force of the spring 13 to the actuation sleeve 26 until the latter by the actuation of the wedge-like slider 108 is deviated through an opening in the guiding sleeve 19 into the niche 121 in the holding piece 63 (FIG. 5). In continuing the movement of the carrier sleeve 28 by the action of the driving spring 13 the carrier bolt 36, on the dosing sleeve 20 (FIG. 4) comes into engagement with the end of the groove in the carrier sleeve 28 and displace axially the dosing sleeve as far as permitted by the dose adjusting stop 34 (FIG. 8). At the beginning of the axial displacement the counter bolt 115 is displaced against a control surface of the cam 116, whereby the spring force on the sliding wedge 114 is relieved and the wedge 114 is pushed back from the area of the driving spring 13. Only upon return of the housing sleeve 20 to its original position and under the action of spring 61 above the piston 1, the cam 116 displaces the counter bolt 115 and thereby the return of the sliding wedge 114 into the area of the spring 13 can be resumed. By removing the finger from the venting attachment 10 the suction chamber 6 is connected with the outer atmosphere and the raised skin portion sucked in the suction cup is released. The cannula is exchanged by means of the protective sleeve and upon repeating of the tensioning process the sealing of the cannula socket 7 is removed. After releasing the tightening screw 120 in the clamping device 40 the dosing rod 9 is pulled back, the swinging arm 118 is swung open and the dosing rod is turned into its rest position in which it is held parallel to the outer housing 50 by means of clamps 119.

Figure 10:
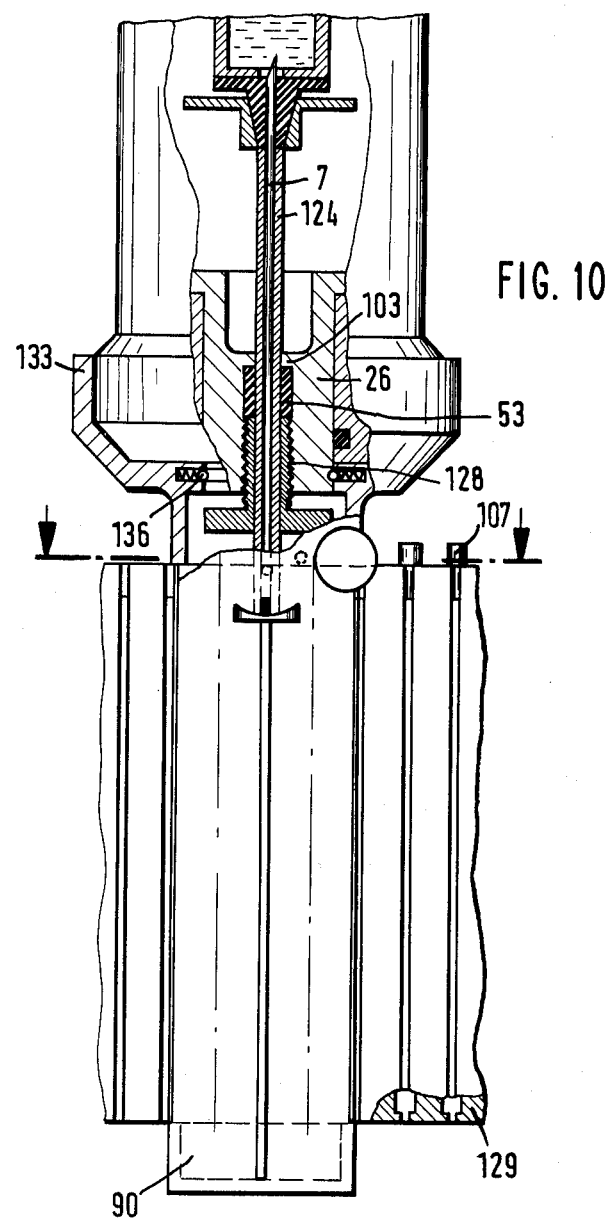
Figure 10B:
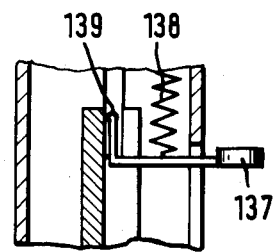
Figure 10A:
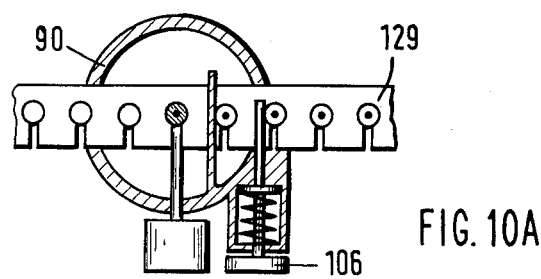

FIG. 10 shows a modification of the suction injector for mounting in the afore-described device cannulas the shaft of which is completely covered with a protecting sleeve 124. The cannula attachment is affected by means of a tapering clamp 128 insertable into a threaded hole in the center of the suction piston 26 and having a central boring for receiving the protective sleeve 124 of the cannula shaft 7. The clamping of the protective sleeve 24 within the boring of the shaft 26 is made by a sealing ring 53 and a holding ring 107. A plurality of cannulas are shiftably arranged side-by-side in a magazine 129 that is attached to the suction cup 133 by means of spring loaded arresting mechanism 136. The arresting mechanism includes locking bolts that engage a groove provided at the end outer surface of the piston 26. A sliding knob 137 is arranged for movement in a slit of the holding arrangement 130 and is held in normal position by means of a pressure spring 138. The free end of the sliding knob 137 has an extension pin 139 that engages an opening in the longitudinal boring for the protective sleeves of cannulas. A spring-biased locking pin 140 acts as a stop member for the series arranged cannulas in the magazine. In using the cannula magazine, the tapering clamp 128 is first screwed out of the piston 26 and the sealing gap in the sealing ring 53 is increased. The slidable magazine 129 is inserted into the cup-shaped holding arrangement 130 and the latter is inserted on a profiled disc 133 on the suction piston 26 whereby a pressure is exerted on the cover cap 5. The locking of the ball arresting mechanism 131 prevents a premature release of the driving spring 13. By activating the sliding knob 137 the spreader pin 139 penetrates an empty protective sleeve 124, the latter sliding through the sealing ring 53 over the cannula taking place in the suction cup. Upon releasing the pressure upon the sliding knob the used cannula together with its protective sleeve 124 is withdrawn by the aid of the spring 138 from the suction cup and reinserted into its original position in the sliding magazine 129. If the locking by the locking pin 140 is relieved, the sliding magazine can be shifted about an interval corresponding to the location of the next cannula.

By repeating pressure on the sliding knob 137 the new cannula is inserted by means of its protecting sleeve 124 into the tapering clamp and advanced through the sealing ring 53 as far as to the cannula socket 7. The cover cap 5 has always to be pressed to lock the sealing ring in the piston 26. Upon relieving the pressure on the sliding knob the protective sleeve on the newly produced cannula is withdrawn into its seat in the sliding magazine and the extension pin 139 is removed from the protective sleeve. Thereupon the holding arrangement 133 is removed from the suction piston 26.

Figure 11:
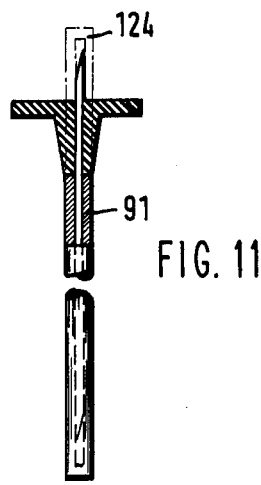
FIGS. 11 to 13 show different embodiment of a cannula for use with the suction injector according to this invention.

FIG. 11 shows a cannula having two obliquely cut end sections, whereby the cannula shaft is provided with a protective sleeve 124 and the upper point of the cannula has just penetrated a seal in the medicine container.

Figure 12:
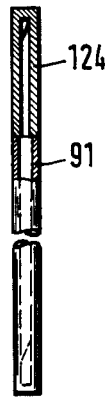

FIG. 12 illustrates a cannula having a stepped shaft with different diameters and being covered with a protective sleeve 124.

Figure 13:

FIG. 13 shows a cannuls shaft having a bulging surface portion that separates a protective sleeve 134 and a handling sleeve 91.

Figure 14:
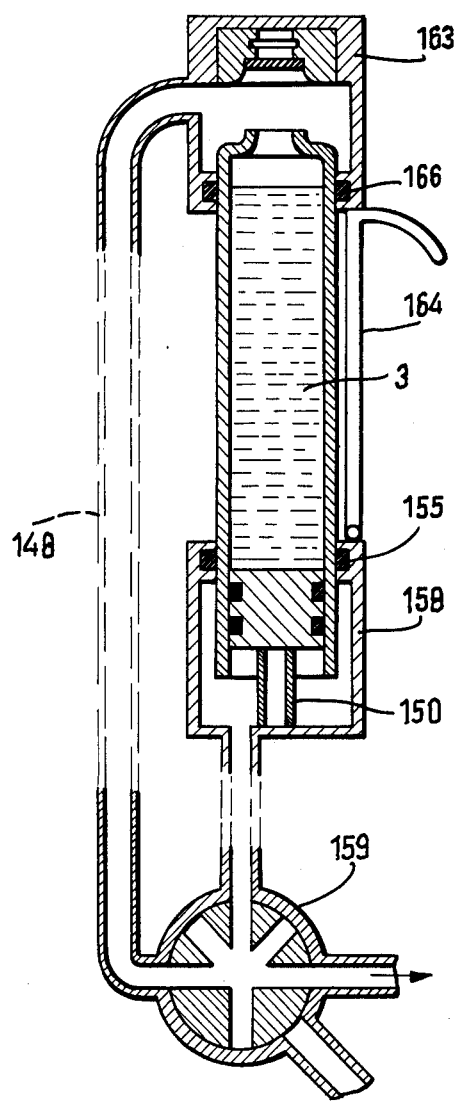
FIGS. 14 to 16 show in a sectional view a medicine charging device for use in connection with a suction injector of this invention.
Figure 15:
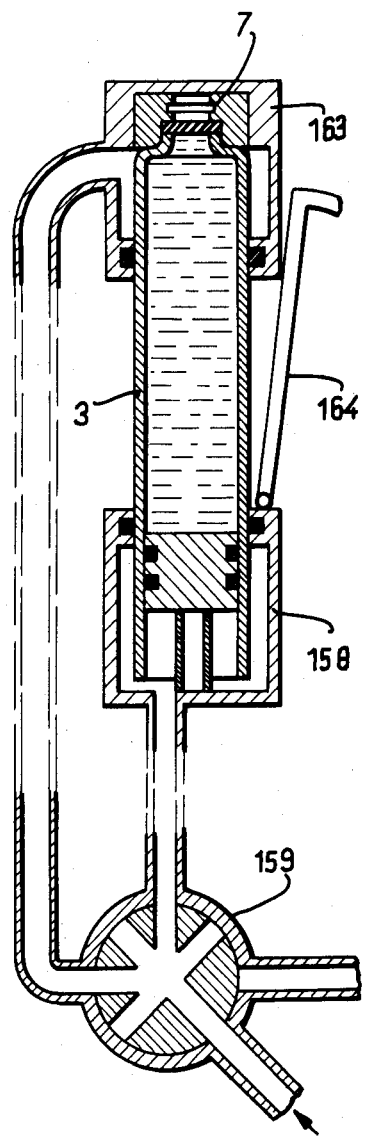
Figure 16:
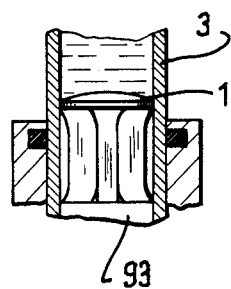

FIGS. 14 to 16 illustrate a device for charging a medicine container 3 with a new medicine. The device consists of an upper sealing cup 158 defining a holding cheek 155 insertable on the open end of the container 3 to be filled with a medicine. A separate lower sealing cap 163 is provided also with a sealing cheek 166 insertable on the outlet end of the container 3 and being provided with a cup-shaped portion for receiving a new cannula socket 7. By means of the upper sealing cap 158, a new piston 1 is inserted into the container 3 by means of a plunger 150. The two sealing caps 158 and 163 are mutually connected by a hose 148 via a two-way valve 159 that controls the filling operation. A hinged bar 164 pivotably mounted on the upper sealing cap 158 prevents the two caps from approaching each other when vacuum is created in the container 3 (FIG. 14). FIG. 15 shows a position when the bar 164 is disengaged from the lower cap 163 and the two caps 163 and 158 rest on the ends of the container 3 and the cannula socket 7 is compressed on the reduced neck of the container.

FIG. 16 shows a modification of the piston 1 in the medicine container 3 connected to a rigid end plate 99 and a dosing rod 93.

It will be understood that each of the elements described above, or two or more together, may also find a useful application in other types of constructions differing from the types described above.

While the invention has been illustrated and described as embodied in a multi-dosage injector for one hand administering metered doses of a medicine to the patient, it is not intended to be limited to the details shown, since various modifications and structural changes may be made without departing in any way from the spirit of the present invention.

What is claimed as new and desired to be protected by Letters Patent is set forth in the appended claims:

1. A suction injector having a dosing mechanism, comprising a tubular container for storing a multiple dose of a liquid medicine; a piston arranged for movement in said container; an exchangeable cannula connected to one end of said container; a container housing adapted for accommodating said container; a suction cup attached to one end portion of said container housing to pull up the skin of a patient against said cannula; an underpressure generator including a pressure gas container and a pump connected to said suction cup, said under-pressure generator being attached to said container housing and communicating with said suction cup; pressure controlling means having a control valve and disposed between said suction cup and said underpressure generator to control the pressure conditions in said suction cup; a non-return valve coupled between said under-pressure generator and said suction cup to maintain under-pressure in said cup when the suction from said pump is interrupted; and a dosing mechanism arranged on said container housing and coupled to said piston in said container to permit an incremental movement of the piston toward said cannula, the end of said container housing opposite said cannula being hermetically sealed by a closure cap and the space resulting between the cap and the upper surface of said piston communicating through said control valve with said pressure gas container in said under pressure generator to move said piston about a predetermined increment.

2. A suction injector as defined in claim 1, wherein a protective folded membrane or bellows is arranged between said closure cap and the upper surface of said piston and the pressure gas conduit opens into the space between said membrane and said closure cap.

3. A suction injector as defined in claim 2, wherein said control valve includes a hand operated main pressure control valve adapted for closing a pressure equalizing conduit connecting said suction cup with the outer atmosphere and opening a pressurized gas conduit from said pressure gas container communicating with said pump, the under-pressure generated by said pump controlling a suction selector to disconnect the suction conduit from said suction cup and apply pressurized gas into said space above said piston.

4. A suction injector as defined in claim 3, wherein said dosing mechanism includes a blind boring provided in said piston, a holding piece secured to the end of said blind boring and having a central boring for accommodating a dosage pin, said dosage pin projecting from said central boring into said blind boring and having at its end an abutment plate supporting a spring extending in said blind boring to said holding piece, and a movement limiting string attached to the end of said dosing pin in said central boring and being guided to a winding roller on said container housing, said winding roller uncoiling by the aid of said spring in said blind boring a predetermined portion of said string corresponding to a stroke of said piston.

5. A suction injector as defined in claim 1, wherein said suction cup has an elastic rim exceeding the tip of said cannula.

6. A suction injector as defined in claim 1 wherein said under pressure generator includes an actuation sleeve surrounding said container housing and being connected at one end to a suction piston arranged in said suction cup and at the other end to a hand operated cover cap for displacing said actuation sleeve in an axial direction.

7. A suction injector as defined in claim 6, further including a carrier sleeve surrounding said actuation sleeve and being connected thereto by a carrier pin, said carrier sleeve being loaded by a driving spring resting in said suction cup and urging said actuation sleeve together with said carrier sleeve into a normal position above said container housing.

8. A suction injector as defined in claim 7, further including a hand-operated arresting mechanism for said actuation sleeve for arresting said actuation sleeve together with said carrier sleeve in a compressed position against said driving spring.

9. A suction injector as defined in claim 8, wherein said driving spring, upon the release of said arresting mechanism, drives said actuation sleeve and said suction piston upwardly to create under pressure in said suction cup.

10. A suction injector as defined in claim 9, wherein said dosing mechanism includes a dosing sleeve, a spring loaded swivel arm tiltably arranged on said dosing sleeve and having a free end thereof connected to a clamping jaw, a dosing rod passing through said clamping jaw and abutting against said piston in said medicine container, said clamping jaw together with said dosing rod being mechanically displaceable to advance said piston about a predetermined increment.

11. A suction injector as defined in claim 10, wherein the suction piston connected to the actuation sleeve projects in the compressed condition of said actuation sleeve above the rim of said suction cup and is withdrawn into said cup by said driving spring.

12. A suction injector as defined in claim 11, further comprising an outer housing and a finger operated venting attachment secured to said outer housing and communicating with the interior of said suction cup via a hose.

13. A suction injector as defined in claim 12, wherein said dosing sleeve is supported on said outer housing and is movable thereon along an axial indexing scale, said swivel arm supported on said housing sleeve being displaceable along said dosing scale to adjust the movement of said dosing rod.

14. A suction injector as defined in claim 13, wherein said dosing mechanism includes a cup-shaped stop piece disposed in said medicine container above said piston and including a pressure spring for limiting the incremental movement of said piston.

15. A suction injector as defined in claim 1 further including a sealing piston arranged for movement in said suction cup and a holding piece provided on said sealin piston for supporting a folded membrane or bellows.

* * * * *